(12) United States Patent
Harn et al.

(10) Patent No.: US 7,799,755 B2
(45) Date of Patent: *Sep. 21, 2010

(54) IMMUNOMODULATORY METHODS USING OLIGOSACCHARIDES

(75) Inventors: Donald A. Harn, Pembroke, MA (US); Palanivel Velupillai, Boston, MA (US)

(73) Assignee: The President and Fellows of Harvard College, Cambridge, MA (US)

( * ) Notice: Subject to any disclaimer, the term of this patent is extended or adjusted under 35 U.S.C. 154(b) by 249 days.

This patent is subject to a terminal disclaimer.

(21) Appl. No.: 11/484,840

(22) Filed: Jul. 11, 2006

(65) Prior Publication Data

US 2007/0149477 A1    Jun. 28, 2007

Related U.S. Application Data

(63) Continuation of application No. 11/033,984, filed on Jan. 11, 2005, now abandoned, which is a continuation of application No. 08/597,518, filed on Jan. 31, 1996, now Pat. No. 6,841,543.

(51) Int. Cl.
*A61K 38/38* (2006.01)
*A61K 31/715* (2006.01)

(52) U.S. Cl. ............................... 514/8; 514/23; 514/54

(58) Field of Classification Search ........................ None
See application file for complete search history.

(56) References Cited

U.S. PATENT DOCUMENTS

| | | | |
|---|---|---|---|
| 5,210,078 | A | 5/1993 | Toyokuni et al. |
| 5,352,670 | A | 10/1994 | Venot et al. |
| 5,426,178 | A | 6/1995 | Laine et al. |
| 5,559,103 | A | 9/1996 | Gaeta et al. |
| 5,580,858 | A | 12/1996 | Ippolito et al. |
| 5,965,544 | A | 10/1999 | Renkonen et al. |

FOREIGN PATENT DOCUMENTS

| | | |
|---|---|---|
| WO | WO-92/04048 A2 | 3/1992 |
| WO | WO-92/22565 A1 | 10/1993 |
| WO | WO-93/21948 A1 | 11/1993 |
| WO | WO-94/11498 A1 | 5/1994 |
| WO | WO-95/27500 A1 | 10/1995 |

OTHER PUBLICATIONS

Richardson, M. et al "Increased expression in vivo of VCAM-1 and E-selectin . . . " Arterioscler. Thromb. (1994) vol. 14, No. 5, pp. 760-769.*

Washington, R. et al "Expression of immunologically relevant endothelial cell activation antigens . . . " Ann. Neurol. (1994) vol. 35, No. 1, pp. 89-97.*

Charlton, B. et al "The Th1/Th2 balance in autoimmunity" Curr. Opin. Immunol. (1995) vol. 7, pp. 793-798.*

Berg, E., et al. "Comparison of L-selectin and E-selectin ligand specificities: the L-selectin can bind the E-selectin ligands sialyl Le(x) and sialyl Le(a)." *Biochem Biophys Res Commun.* Apr. 30, 1992;184(2):1048-55.

Fenderson, B., et al. "A multivalent lacto-N-fucopentaose III-lysyllysine conjugate decompacts preimplantation mouse embryos, while the free oligosaccharide is ineffective." *J Exp Med.* Nov. 1, 1984;160(5):1591-6.

Fortune, F., et al. "The expression of carbohydrate antigens in activated T cells and in autoimmune diseases." *Scand J Immunol.* Dec. 1994;40(6):636-42.

Foxall, C., et al. "The three members of the selectin receptor family recognize a common carbohydrate epitope, the sialyl Lewis(x) oligosaccharide." *J Cell Biol.* May 1992;117(4):895-902.

Hakomori, S. "Le(X) and related structures as adhesion molecules." *Histochem J.* Nov. 1992;24(11):771-6.

Halpern, M., et al. "Modulation of a human immunosuppressive lymphokine by monosaccharides." *Cell Immunol.* Aug. 1991;136(1):29-40.

Harn, D. A. et al., "Regulation of $CD4^+$ T-Cell Subsets in Schistosomiasis: Specific Oligosaccharides Stimulate $B220_+$ Spleen Cells to Proliferate and Secrete IL-10 and Also are Responsible for Recruitment of Peritoneal B-1 Cells", Abstract for *11th Annual Meharry Medical College Symposium*, (Apr. 4, 1994).

(Continued)

*Primary Examiner*—Leigh C Maier
(74) *Attorney, Agent, or Firm*—Lahive & Cockfield, LLP; Giulio A. DeConti, Jr., Esq.; Cynthia L. Kanik

(57) ABSTRACT

Methods for modulating immune responses are provided. The methods involve contacting an immune cell with an agent that modulates interaction of a compound comprising a Lewis antigen with the immune cell such that production by the immune cell of at least one cytokine that regulates development of a T helper type 1 or T helper type 2 response is modulated. In one embodiment, the agent is a stimulatory form of a compound comprising a Lewis antigen, such as a $Lewis^y$, $Lewis^x$ or $Lewis^a$ oligosaccharide, or a derivative thereof. In another embodiment, the agent is an inhibitory form of a compound comprising a Lewis antigen, such as a $Lewis^y$, $Lewis^x$ or $Lewis^a$ oligosaccharide, or a derivative thereof. In various embodiments, the immune cell is a human immune cell, a macrophage or a T cell. Pharmaceutical compositions for modulating immune responses are also provided.

18 Claims, 3 Drawing Sheets

OTHER PUBLICATIONS

Harn, D. A. et al., "LNFPIII Elevates B-1 Cells in the Peritoneal Cavity and May Indirectly Regulate CD4+ T-Cells", *The FASEB Journal*, vol. 8, No. 4, Abstract 2725 (1994).

Kageshita, T., et al. "Association between sialyl Lewis(a) expression and tumor progression in melanoma." *Cancer Res.* Apr. 15, 1995;55(8):1748-51.

Kitamura, K., et al. "Specificity analysis of blood group Lewis-y (Le(y)) antibodies generatedagainst synthetic and natural Le(y) determinants." *Proc Natl Acad Sci U S A*. Dec. 20, 1994;91(26):12957-61.

Ko, A., et al. "A *Schistosoma mansoni* epitope recognized by a protective monoclonal antibody is identical to the stage-specific embryonic antigen 1." *Proc Natl Acad Sci U S A*. Jun. 1990;87(11):4159-63.

Kokai, M., et al. "Elevated Le(y) antigen expression on T-lymphocytes in schizophrenic patients." *Eur Arch Psychiatry Clin Neurosci.* 1993;243(2):82-6.

Kuchroo, V., et al. "B7-1 and B7-2 costimulatory molecules activate differentially the Th1/Th2 developmental pathways: application to autoimmune disease therapy." *Cell.* Mar. 10, 1995;80(5):707-18.

Martensson, S., et al. "Sialyl-Lewis(x) and related carbohydrate antigens in the prostate." *Hum Pathol.* Jul. 1995;26(7):735-9.

Moore, K., et al. "Interleukin-10." *Annu Rev Immunol.* 1993;11:165-90.

Muguruma, M., et al. "Hepatic neoexpression and increased plasma levels of Lewis Y, a carbohydrate antigen, in chronic inflammatory liver diseases." *Am J Clin Pathol.* Aug. 1994;102(2):176-81.

Ohta, S., et al. Tumor-associated glycoantigen, sialyl Lewis(a) as a target for bispecific antibody-directed adoptive tumor immunotherapy. Immunol Lett. Jan. 1995;44(1):35-40.

Okada, Y., et al. "Neoexpression of sialyl oligomeric Lewis X by Kupffer cells in chronic hepatitis." *Lancet.* Jun. 2, 1990;335(8701):1302-6.

Paavonen, T., et al. "Selective expression of sialyl-Lewis x and Lewis a epitopes, putative ligands for L-selectin, on peripheral lymph-node high endothelial venules." *Am J Pathol.* Dec. 1992;141(6):1259-64.

Ryan, C.A. "Oligosaccharide signals: from plant defense to parasite offense." *Proc Natl Acad Sci U S A.* Jan. 4, 1994;91(1):1-2.

Tyrrell, D., et al. "Structural requirements for the carbohydrate ligand of E-selectin." *Proc Natl Acad Sci U S A.* Nov. 15, 1991;88(22):10372-6.

Van Dam, G., et al. "The immunologically reactive O-linked polysaccharide chains derived from circulating cathodic antigen isolated from the human blood fluke *Schistosoma mansoni* have Lewis x as repeating unit." *Eur J Biochem.* Oct. 1, 1994;225(1):467-82.

Velupillai, P., et al. "Oligosaccharide Interactions with Mononuclear Cells from Mice Infected with *Schistosoma Mansoni* or *Trypanosoma Cruzi* May Lead to CD4+ T Cell Subset Regulation", Abstract for Am. Soc. of Tropical Medicine and Hygiene Meeting (Nov. 1993).

Velupillai, P., et al., "Recombinant Murine IL-12 Inhibits Ligand-Specific Recruitment of Peritoneal B220+, CD5+ (B-1) Cells", Abstract for Clinical Immunology Meeting (Apr. 1994).

Velupillai, P., et al. "Oligosaccharide-specific induction of interleukin 10 production by B220+ cells from schistosome-infected mice: a mechanism for regulation of CD4+ T-cell subsets." *Proc Natl Acad Sci U S A.* Jan. 4, 1994;91(1):18-22.

Velupillai, P., et al. "Interleukin-12 and -10 and gamma interferon regulate polyclonal and ligand-specific expansion of murine B-1 cells." *Infect Immun.* Nov. 1996;64(11):4557-60.

Velupillai, P., et al. "Lewis(x)-containing oligosaccharide attenuates schistosome egg antigen-induced immune depression in human schistosomiasis." *Hum Immunol.* Mar. 2000;61(3):225-32.

Williams, M., et al. "Leukocytes of patients with *Schistosoma mansoni* respond with a Th2 pattern of cytokine production to mitogen or egg antigens but with a Th0 pattern to worm antigens." *J Infect Dis.* Oct. 1994;170(4):946-54.

\* cited by examiner

IMMUNOMODULATORY METHODS USING OLIGOSACCHARIDES

RELATED APPLICATION

This application is a continuation of U.S. application Ser. No. 11/033984 filed Jan. 11, 2005, which is a continuation of U.S. application Ser. No. 08/597518 filed Jan. 31, 1996 (now U.S. Pat. No. 6,841,543, issued Jan. 11, 2005), the entire contents of which are hereby incorporated by reference.

GOVERNMENT FUNDING

Work described herein was supported under grant AI 27448 awarded by the National Institutes of Health. The U.S. government therefore may have certain rights in this invention.

BACKGROUND OF THE INVENTION

The T lymphocyte compartment of the immune system can be divided into a variety of cell subsets. For example, $CD4^+$ T cells represent the T helper cell subset, whereas $CD8^+$ T cells represent the cytotoxic T cell subset. Additionally, $CD4^+$ T helper cells mature into distinct subpopulations that produce different panels of cytokines: the T helper type 1 (Th1) subset produces interleukin-2 (IL-2), interferon-$\gamma$ (IFN-$\gamma$) and tumor necrosis factor-$\beta$ (TNF-$\beta$), whereas the T helper type 2 (Th2) subset produces interleukin-4 (IL-4), interleukin-5 (IL-5), interleukin-6 (IL-6) and interleukin-10 (IL-10). The Th1 and Th2 subsets also have differing functional activities. Th1 cells are involved in inducing delayed type hypersensitivity responses, whereas Th2 cells are involved in providing efficient "help" to B lymphocytes and stimulate production of IgG1 and IgE antibodies. For a review of Th1 and Th2 subsets, see Seder, R. A. and Paul, W. E. (1994) *Ann. Rev. Immunol.* 12:635-673.

Cytokines are thought to play a dominant role in controlling the differentiation of T helper precursors (Thp) to either the Th1 or Th2 lineage. Th1-associated cytokines, such as IFN-$\gamma$, can enhance the development of Th1 cells and inhibit the development of Th2 cells, whereas Th2-associated cytokines, such as IL-4 and IL-10, can enhance the development of Th2 cells and inhibit the development of Th1 cells. Thus, cytokines can reciprocally regulate the development and/or progression of either a Th1 or a Th2 response.

The course of certain disease states is influenced by whether a predominant Th1 response or Th2 response is mounted. For example, in experimental leishmania infections in mice, animals that are resistant to infection mount predominantly a Th1 response, whereas animals that are susceptible to progressive infection mount predominantly a Th2 response (Heinzel, F. P., et al. (1989) *J. Exp. Med.* 169:59-72; Locksley, R. M. and Scott, P. (1992) *Immunoparasitology Today* 1:A58-A61). In murine schistosomiasis, a Th1 to Th2 switch is observed coincident with the release of eggs into the tissues by female parasites and is associated with a worsening of the disease condition (Pearce, E. J., et al. (1991) *J. Exp. Med.* 173:159-166; Grzych, J-M., et al. (1991) *J. Immunol.* 141:1322-1327; Kullberg, M. C., et al. (1992) *J. Immunol.* 148:3264-3270). Many human diseases, including chronic infections (such as with human immunodeficiency virus (HIV) or tuberculosis) and certain metastatic carcinomas, also are characterized by a Th1 to Th2 switch, with elevated expression of IL-10 (see e.g., Shearer, G. M. and Clerici, M. (1992) *Prog. Chem. Immunol.* 54:21-43; Clerici, M and Shearer, G. M. (1993) *Immunology Today* 14:107-111; Yamamura, M., et al. (1993) *J. Clin. Invest.* 91:1005-1010; Pisa, P., et al. (1992) *Proc. Natl. Acad. Sci. USA* 89:7708-7712; Fauci, A. S. (1988) *Science* 239:617-623). Furthermore, certain autoimmune diseases have been shown to be associated with a predominant Th1 response. For example, patients with rheumatoid arthritis have predominantly Th1 cells in synovial tissue (Simon, A. K., et al. (1994) *Proc. Natl. Acad. Sci. USA* 91:8562-8566) and experimental autoimmune encephalomyelitis (EAE) can be induced by autoreactive Th1 cells (Kuchroo, V. K., et al. (1993) *J. Immunol.* 151:4371-4381).

Velupillai and Ham (*Proc. Natl. Acad. Sci. USA* (1994) 91:18-22) have shown that schistosome egg antigen (SEA), which expresses the Lewis$^x$ antigen, and conjugates of the Lewis$^x$ antigen, can stimulate IL-10 production by B cells from *Schistosoma mansoni* infected mice, but not B cells from uninfected mice, suggesting that during the course of *S. mansoni* infection, the observed Th1 to Th2 shift may results from IL-10 production by B cells induced by SEA. This work, however, did not demonstrate whether human immune cells (e.g., human immune cells in the absence of *S. mansoni* infection) were responsive to Lewis antigen-containing compounds, nor whether cell types other than B cells, such as macrophages or T cells, could produce IL-10 in response to stimulation with compounds comprising a Lewis antigen in the absence of *S. mansoni* infection. Moreover, this work did not demonstrate whether production other cytokines that regulate development of Th1 and Th2 responses, such as IL-4, could be stimulated

SUMMARY OF THE INVENTION

Given the role of either Th1 or Th2 cells in the development or progression of many disease states, methods for influencing whether a Th1 or Th2 response is mounted are desirable for a variety of clinical situations. This invention provide methods for modulating immune responses by modulating the interaction of immune cells with a compound comprising a Lewis antigen such that production by the immune cells of at least one cytokine that regulates development of a Th1 or Th2 response is modulated. The invention is based, at least in part, on the discovery that stimulation of human immune cells, T cells or macrophages with Lewis antigen-containing conjugates results in the production of cytokines that regulate the development of Th1 or a Th2 response. Moreover, it has now been discovered that human immune cells are sensitive to stimulation by Lewis$^y$ antigen-containing conjugates, that cells from human allergy patients and cancer patients show responsiveness to Lewis antigens, that IL-4 production can be stimulated by Lewis antigen-containing conjugates and that conjugates wherein the sugars represent approximately 20-24% of the conjugate by weight, or greater, are preferred for stimulation. The immunomodulatory methods of the invention allow for an immune response to be directed to either a Th1 or a Th2 response. The ability to influence the development of either a Th1 or a Th2 response using the immunomodulatory methods of the invention is applicable to the treatment of a wide variety of disorders, including cancer, infectious diseases (e.g., HIV and tuberculosis), allergies and autoimmune diseases.

In one embodiment, the invention provides an immunomodulatory method comprising contacting a human immune cell with an agent that modulates interaction of a compound comprising a Lewis antigen with the human immune cell such that production by the human immune cell of at least one cytokine that regulates development of a Th1 or Th2 response is modulated. The human immune cell can be, for example, a T cell, a macrophage or a B cell. In another embodiment, the invention provides an immunomodulatory method comprising contacting a macrophage with an agent that modulates interaction of a compound comprising a Lewis antigen with the macrophage such that production by the macrophage of at least one cytokine that regulates development of a Th1 or Th2 response is modulated. In yet another embodiment, the invention provides an immunomodulatory method comprising contacting a T cell with an agent that modulates interaction of a compound comprising a Lewis antigen with the T cell such that production by the T cell of at least one cytokine that regulates development of a Th1 or Th2 response is modulated.

In one embodiment of the immunomodulatory methods of the invention, production by immune cells of at least one cytokine (preferably IL-10 or IL-4) that regulates development of a Th1 or Th2 response is stimulated. In this embodiment, the agent with which the immune cells are contacted preferably is a stimulatory form of a compound comprising a Lewis antigen, such as a compound comprising cross-linked (i.e., multivalent) $Lewis^y$ oligosaccharides, $Lewis^x$ oligosaccharides, $Lewis^a$ oligosaccharides or derivatives thereof (e.g., sulfated, sialylated or sulfo-sialylated forms of these oligosaccharides). The stimulatory compound can be, for example, a conjugate of the Lewis antigen and a carrier molecule (e.g., human serum albumin or polyacrylamide). For stimulating responses by human immune cells, the agent preferably comprises a $Lewis^y$ oligosaccharide or a derivative thereof.

In another embodiment of the immunomodulatory methods of the invention, production by immune cells of at least one cytokine (preferably IL-10 or IL-4) that regulates development of a Th1 or Th2 response is inhibited. In this embodiment, the agent with which the immune cells are contacted preferably is an inhibitory form of a compound comprising a Lewis antigen, such as a soluble, monovalent (i.e., non-crosslinked) form of a $Lewis^y$ oligosaccharide, a $Lewis^x$ oligosaccharide, a $Lewis^a$ oligosaccharide or a derivative thereof (e.g., sulfated, sialylated or sulfo-sialylated forms of these oligosaccharides). For inhibiting responses by human immune cells, the agent preferably comprises a $Lewis^y$ oligosaccharide or a derivative thereof.

The stimulatory or inhibitory compounds of the invention can be contacted with immune cells in vitro to produce one or more cytokines that regulate the development of a Th1 or Th2 response. After in vitro stimulation, the immune cells can be administered to a subject to influence whether a Th1 or a Th2 response predominates in the subject. Alternatively, a stimulatory or inhibitory compound of the invention can be administered to a subject such that production of at least one cytokine that regulates development of a Th1 or Th2 response is either stimulated or inhibited, respectively, in the subject, thereby influencing whether a Th1 or a Th2 response predominates in the subject. Accordingly, another aspect of the invention pertains to pharmaceutical compositions suitable for pharmaceutical administration. The pharmaceutical compositions of the invention typically comprise a stimulatory or inhibitory agent of the invention (e.g., a compound comprising a Lewis antigen) and a pharmaceutically acceptable carrier. In one embodiment, the composition is formulated to modulate responses by human immune cells. In this embodiment, the active agent preferably comprises a $Lewis^y$ oligosaccharide. In another embodiment, the composition is formulated to modulate responses by macrophages. In yet another embodiment, the composition is formulated to modulate responses by T cells.

DETAILED DESCRIPTION OF THE INVENTION

Figure 1:
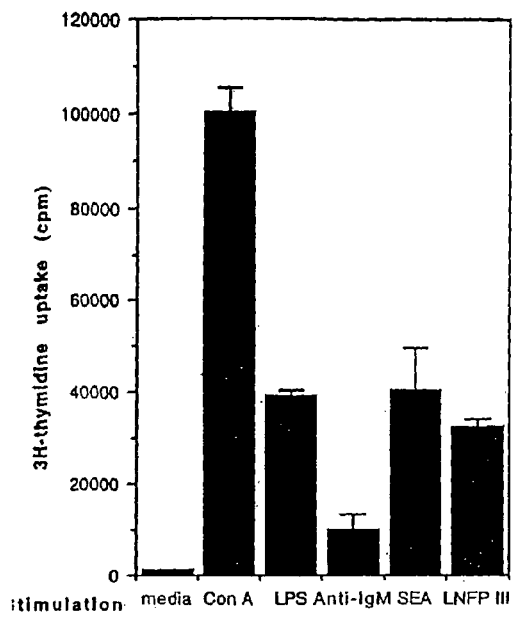
FIG. 1A is a bar graph depicting the proliferation of splenocytes from S. mansoni infected mice when stimulated with either media alone, Con A, LPS. anti-IgM, SEA or LNFP III conjugated to HSA.
FIG. 1B is a graph depicting the proliferation of splenocytes from S. mansoni infected mice when stimulated with increasing amounts of either $Lewis^a$ antigen, $Lewis^x$ antigen, sialyl-$Lewis^x$ antigen or sialyl-$Lewis^a$ antigen, each conjugated to polyacrylamide.
FIG. 1C is a bar graph depicting the proliferation of splenocytes from uninfected mice when stimulated with either media alone, Con A, LPS. anti-IgM, SEA or LNFP III conjugated to HSA.
FIG. 1D is a graph depicting the proliferation of splenocytes from uninfected mice when stimulated with increasing amounts of either $Lewis^a$ antigen, $Lewis^x$ antigen, sialyl-$Lewis^x$ antigen or sialyl-$Lewis^a$ antigen, each conjugated to polyacrylamide.
Figure 1:
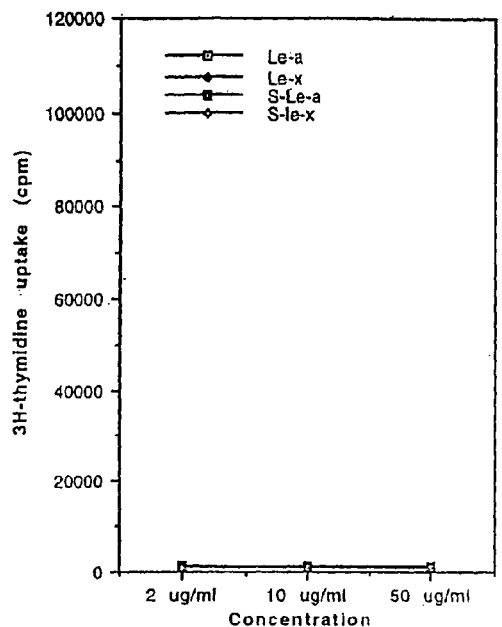
Figure 1:
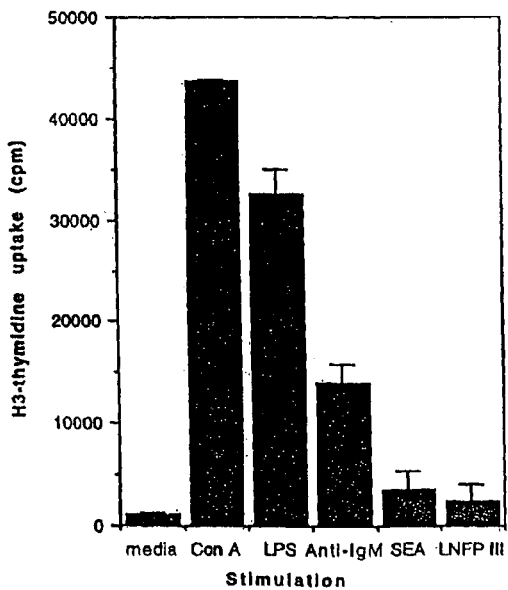
Figure 1:
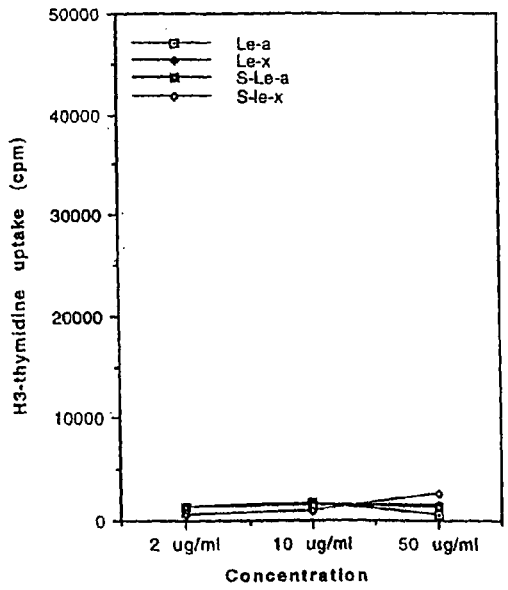

This invention provides immunomodulatory methods in which a cell (e.g., a human immune cell, a macrophage or a T cell) is contacted with an agent which modulates production by the cell of one or more cytokines that regulate Th1 or Th2 responses. The invention is based, at least in part, on the discovery that when human immune cells, macrophages or T cells are stimulated with a multivalent, crosslinked form of a Lewis antigen, the cells produce one or more cytokines (such as IL-10 and/or IL-4) that promote the development of a Th2 response and inhibit the development of a Th1 response. Human immune cells that exhibit this responsiveness include T cells from a pollen allergic individual and peripheral blood mononuclear cells from individuals with colon or lung carcinomas or B lymphoma. Moreover, it has now been discovered that human immune cells preferentially respond to compounds comprising a Lewis$^y$ oligosaccharides. Still further, it has now been discovered that Lewis antigens conjugated to a carrier at a ligand density such that the sugars represent approximately 20-24% of the conjugate by weight are especially effective at stimulating production of cytokines that promote the development of a Th2 response (e.g., IL-10 and IL-4), an in particular can stimulate IL-4 production by splenocytes of uninfected subjects. A preferred carrier for such stimulatory conjugates is polyacrylamide.

In contrast to these stimulatory methods, contact of the cells with a monovalent, non-crosslinked form of the Lewis antigen inhibits the production of cytokines that promote Th2 responses and downregulate Th1 responses that normally are produced when the cells encounter a stimulatory form of a Lewis antigen. Thus, the methods of the invention allow for cytokine production either to be stimulated or inhibited, depending on whether a stimulatory agent or an inhibitory agent is used. Accordingly, the immunomodulatory methods of the invention allow for an immune response to be directed to either a Th1 or a Th2 response. The ability to influence the development of either a Th1 or a Th2 response using the immunomodulatory methods of the invention is applicable to the treatment of a wide variety of disorders, including cancer, infectious diseases (e.g., HIV and tuberculosis), allergies and autoimmune diseases.

In order that the present invention may be more readily understood, certain terms are first defined. Standard abbreviations for sugars are used herein.

As used herein, the term "Lewis antigen" is intended to include carbohydrates having as a core sequence either the lacto type I structure {Gal($\beta$1-3)GlcNac} or the lacto type II structure {Gal($\beta$1-4)GlcNac}, substituted with one or more fucosyl residues. The Lewis antigen may comprise a single substituted core sequence or a repetitive series of substituted core sequences. Moreover, the core sequence may be present within a larger sugar. Accordingly, a Lewis antigen-containing oligosaccharide can be, for example, a trisaccharide, a tetrasaccharide, a pentasaccharide, and so on. Types of Lewis antigens include Lewis$^x$, Lewis$^y$, Lewis$^a$ and Lewis$^b$ oligosaccharides and derivatives thereof. Synthetic structural homologues of these carbohydrates that retain the immunomodulatory capacity described herein are also intended to be encompassed by the term "Lewis antigen".

As used herein, the term "Lewis$^x$ oligosaccharide" refers to a lacto type II carbohydrate comprising the structure: {Gal($\beta$1-4)[Fuc($\alpha$1-3)]GlcNac}.

As used herein, the term "Lewis$^y$ oligosaccharide" refers to a lacto type II carbohydrate comprising the structure: {Fuc($\alpha$1-2)Gal($\beta$1-4)[Fuc($\alpha$1-3)]GlcNac}.

As used herein, the term "Lewis$^a$ oligosaccharide" refers to a lacto type I carbohydrate comprising the structure: {Gal($\beta$1-3)[Fuc($\alpha$1-4)]GlcNac}.

As used herein, the term "Lewis$^b$ oligosaccharide" refers to a lacto type I carbohydrate comprising the structure: {Fuc($\alpha$1-2)Gal($\beta$1-3)[Fuc($\alpha$1-4)]GlcNac}.

As used herein, a "derivative" of a Lewis oligosaccharide refers to a Lewis oligosaccharide having one or more additional substituent groups. Examples of derivatives include terminally sialylated forms of Lewis oligosaccharides (e.g., sialyl-Lewis$^x$, sialyl-Lewis$^y$, sialyl-Lewis$^a$, sialyl-Lewis$^b$), sulfated forms of Lewis oligosaccharides and sulfo-sialylated forms of Lewis oligosaccharides.

As used herein, the term "human immune cell" is intended to include cells of the human immune cell which are capable of producing cytokines that regulate the development of a Th1 or Th2 response. Examples of human immune cells include human T cells, human macrophages and human B cells.

As used herein, the term "macrophage" is intended to include all cells within the macrophage lineage, including monocytes, circulating macrophages, tissue macrophages, activated macrophages, and the like, from a mammal (e.g., human or mouse).

As used herein, the term "T cell" (i.e., T lymphocyte) is intended to include all cells within the T cell lineage, including thymocytes, immature T cells, mature T cells and the like, from a mammal (e.g., human or mouse).

As used herein, a "T helper type 2 response" (Th2 response) refers to a response by CD4$^+$ T cells that is characterized by the production of one or more cytokines selected from IL-4, IL-5, IL-6 and IL-10, and that is associated with efficient B cell "help" provided by the Th2 cells (e.g., enhanced IgG1 and/or IgE production).

As used herein, a "T helper type 1 response" (Th1 response) refers to a response by CD4$^+$ T cells that is characterized by the production of one or more cytokines selected from IL-2, IFN-g and TNF-$\beta$, and that is associated with delayed type hypersensitivity responses.

As used herein, the term "a cytokine that regulates development of a Th1 or Th2 response" is intended to include cytokines (produced by Th1 or Th2 cells or other cell types), that have a positive or negative effect on the initiation and/or progression of a Th1 or Th2 response, and especially those cytokines that have reciprocal effects on the development of the Th1 vs. Th2 subpopulations, in particular, cytokines that promote the development of a Th2 response and downregulate the development of a Th1 response. Preferred cytokines that are produced by the methods of the invention are IL-10, IL-4 and prostaglandin E$_2$ (PGE$_2$). The most preferred cytokine produced by the methods of the invention is IL-10.

As used herein, the term "development of a Th1 or Th2 response" is intended to include initiation of either a Th1 or Th2 response (e.g., commitment of T helper precursors to either the Th1 or Th2 lineage) and progression of either a Th1 or Th2 response (e.g., further differentiation of cells to either the Th1 or Th2 phenotype and/or continued function of Th1 or Th2 cells during an ongoing immune response). Thus, a cytokine(s) produced in accordance with the methods of the invention may have an effect on the initiation of a Th1 or Th2 response, the progression of a Th1or Th2 response, or both.

As used herein, the various forms of the term "modulation" are intended to include stimulation (e.g., increasing or upregulating a particular response or activity) and inhibition (e.g., decreasing or downregulating a particular response or activity).

As used herein, the term "contacting" (i.e., contacting an agent with a cell) is intended to include incubating the agent and the cell together in vitro (e.g., adding the agent to cells in culture) and administering the agent to a subject such that the agent and cells of the subject are contacted in vivo.

Various aspects of the invention are described in further detail in the following subsections.

I. Immunomodulatory Agents

In the immunomodulatory methods of the invention, a cell (e.g., a human immune cell, macrophage or T cell) is contacted with an agent that modulates interaction of a compound comprising a Lewis antigen with the cell such that production by the cell of at least one cytokine that regulates development of a Th1 or Th2 response is modulated. Preferably, the agent itself comprises a Lewis antigen, as described in further detail below. In one embodiment, the agent is a "stimulatory agent", which stimulates production by the cell of at least one cytokine that regulates development of a Th1 or Th2 response. In another embodiment, the agent is an "inhibitory agent", which inhibits production by the cell of at least one cytokine that regulates development of a Th1 or Th2 response (i.e., the inhibitory agent can block the production of cytokines that normally occurs when the cell encounters a stimulatory form of a Lewis antigen).

A. Stimulatory Agents

The stimulatory agents of the invention stimulate production by cells (e.g., human immune cells, macrophages or T cells) of at least one cytokine that regulates development of a Th1 or Th2 response. In a preferred embodiment, the stimulatory agent is a stimulatory form of a compound comprising a Lewis antigen. A "stimulatory form of a compound comprising a Lewis antigen" typically is one in which the carbohydrate structure is present in a multivalent, crosslinked form. In a preferred embodiment, the stimulatory form of a compound comprising a Lewis antigen is a conjugate of a carrier molecule and multiple carbohydrate molecules expressing a Lewis antigen. For example, carbohydrate molecules can be conjugated to a protein carrier, such as a conjugate of human serum albumin (HSA) and Lewis$^y$ oligosaccharides (referred to herein as HSA-Le$^y$). When a sugar-carrier protein conjugate is to be administered to a subject, the carrier protein should be selected such that an immunological reaction to the carrier protein is not stimulated in the subject (e.g., a human carrier protein should be used with a human subject, etc.). Alternative to a carrier protein, multiple Lewis antigens can be conjugated to other carrier molecules, such as a solid support, such as beads (e.g., polyacrylamide, agarose, sepharose, polystyrene and the like) or a plate. The degree of stimulatory ability of the conjugate is influenced by the density of sugars conjugated to the carrier (see Example 4). Preferably, the sugar molecules comprise at least 10-25% of the conjugate by weight, more preferably at least 15-25% of the conjugate by weight and even more preferably at least 20-25% of the conjugate by weight. In a preferred embodiment, the stimulatory form of a compound comprising a Lewis antigen is a conjugate of multiple carbohydrate molecules expressing a Lewis antigen and the carrier polyacrylamide. More preferably, the polyacrylamide conjugates comprise 25 to 30 (or more) sugars/conjugate, wherein the average molecular weight of the conjugate is approximately 30 kD.

The Lewis antigens present in the conjugate can be, for example, Lewis$^y$, Lewis$^x$, Lewis$^a$ or Lewis$^b$ oligosaccharides, or derivatives thereof. For stimulation of human cells, the stimulatory agent preferably comprises Lewis$^y$ oligosaccharides or derivatives thereof. Within the stimulatory agent, the Lewis antigen can be present within a larger carbohydrate structure. For example, the carbohydrate portion of the stimulatory agent can be lacto-N-fucopentaose III (LNFP-III), which has the structure: {Gal($\beta$1-4)[Fuc($\alpha$1-3)]GlcNac($\beta$1-3)Gal($\beta$1-4)Glc} and comprises the Lewis$^x$ oligosaccharide, or lacto-N-difucohexose I (LND), which has the structure: {Fuc($\beta$1-2)Gal($\beta$1-3)[Fuc($\beta$1-4)]GlcNac($\beta$1-3)Gal($\beta$1-4)Glc} and comprises the Lewis$^b$ oligosaccharide. Other related carbohydrates comprising Lewis antigens that are suitable for use in a stimulatory agent of the invention will be apparent to those skilled in the art.

In addition to conjugates comprising Lewis antigen-containing sugars described above, another form of a stimulatory agent comprising a Lewis antigen is an isolated protein that naturally expresses Lewis antigens in a form suitable for stimulatory activity. One example of such a protein is schistosome egg antigen (SEA), which expresses the Lewis$^x$ oligosaccharide. Other proteins that have been reported to express Lewis antigens include tumor-associated antigens (see e.g., Pauli, B. U., et al. (1992) *Trends in Glycoscience and Glycotechnology* 4:405-414; Hakomori, S-I. (1989) *Adv. Cancer Res.* 52:257-331) and HIV gp120 (Adachi, M., et al. (1988) *J. Exp. Med.* 167:323-331).

Stimulatory agents for use in the methods of the invention can be purchased commercially or can be purified or synthesized by standard methods. Conjugates of Lewis antigen-containing sugars and a carrier protein (e.g., HSA) are available from Accurate Chemicals, Westbury, N.Y. Conjugates of Lewis antigen-containing sugars and polyacrylamide are available from GlycoTech, Rockville, Md. Schistosome egg antigen (SEA) can be purified from *Schistosoma mansoni* eggs as described in Harn, D. H., et al. (1984) *J. Exp. Med.* 159:1371-1387. Lewis antigen-containing sugars, or derivatives thereof, can be conjugated to a carrier protein or solid support (e.g., beads or a plate) by standard methods, for example using a chemical cross-linking agent. A wide variety of bifunctional or polyfunctional cross-linking reagents, both homo- and heterofunctional, are known in the art and are commercially available (e.g., Pierce Chemical Co., Rockford, Ill.).

The ability of a stimulatory agent of the invention to stimulate production by immune cells of at least one cytokine that regulates a Th1 or Th2 response can be evaluated using an in vitro culture system such as that described in the Examples. Cells (e.g., peripheral blood mononuclear cells) are cultured in the presence of the stimulatory agent to be evaluated (e.g., at a concentration of 100 μM for sugar conjugates) in a medium suitable for culture of the chosen cells. After a period of time (e.g., 24-72 hours), production of a cytokine that regulates development of a Th1 or Th2 response is assessed by determining the level of the cytokine in the culture supernatant. Preferably, the cytokine assayed is IL-10. Additionally or alternatively, IL-4 and/or PGE$_2$ levels can be assessed. Cytokine levels in the culture supernatant can be measured by standard methods, such as by an enzyme linked immunosorbent assay (ELISA) utilizing a monoclonal antibody that specifically binds the cytokine. An ELISA for measuring IL-10 levels is described further in Kullberg, M. C., et al. (1992) *J. Immunol.* 148:3264-3270. An ELISA kit for measuring PGE$_2$ levels is commercially available from Advanced Magnetics, Cambridge, Mass. The ability of a stimulatory agent to stimulate cytokine production is evidenced by a higher level of cytokine (e.g., IL-10) in the supernatants of cells cultured in the presence of the stimulatory agent compared to the level of cytokine in the supernatant of cells cultured on the absence of the stimulatory agent.

B. Inhibitory Agents

The inhibitory agents of the invention inhibit production by cells (e.g., T cells, macrophages or human immune cells) of at least one cytokine that regulates development of a Th1 or Th2 response. More specifically, cytokine production by a cell that normally occurs when the cell encounters a stimulatory form of a Lewis antigen can be inhibited by contacting the cell with an inhibitory agent of the invention (i.e., the inhibitory agents of the invention act as blocking agents to inhibit cytokine production that normally would result from interaction of the cell with a stimulatory form of a Lewis antigen). In a preferred embodiment, the inhibitory agent is an inhibitory form of a compound comprising a Lewis antigen. A "inhibitory form of a compound comprising a Lewis antigen" typically is one in which the carbohydrate structure is present in a monovalent, non-crosslinked form. Preferred inhibitory agents are soluble, "free" sugars comprising a Lewis antigen. The Lewis antigen expressed by the inhibitory agent can be, for example, a Lewis$^y$, Lewis$^x$, Lewis$^a$ or Lewis$^b$ oligosaccharide (a single substituted core sequence or a repetitive series of substituted core sequences) or derivatives thereof. For inhibition of human cells, the inhibitory agent preferably comprises a Lewis$^y$ oligosaccharide or a derivative thereof. Within the inhibitory agent, the Lewis antigen can be present within a larger carbohydrate structure. For example, the carbohydrate portion of the inhibitory agent can be lacto-N-fucopentaose III (LNFP-III), which has the structure: {Gal(β1-4)[Fuc(α1-3)]GlcNac(β1-3)Gal(β1-4)Glc} and comprises the Lewis$^x$ oligosaccharide, or lacto-N-difucohexose I (LND), which has the structure: {Fuc(α1-2)Gal(β1-3)[Fuc(α1-4)]GlcNac(β1-3)Gal(β1-4)Glc } and comprises the Lewis$^b$ oligosaccharide. Other related carbohydrates comprising Lewis antigens that are suitable for use in an inhibitory agent of the invention will be apparent to those skilled in the art. Soluble, free sugars comprising a Lewis antigen for use as inhibitory agents can be purchased commercially or synthesized by standard methods (as described above).

In addition to free sugars comprising Lewis antigens, another form of an inhibitory agent is an antibody to a Lewis antigen. Polyclonal antibodies, or more preferably monoclonal antibodies (mAbs), that specifically bind a Lewis antigen (e.g., a Lewis$^y$, Lewis$^x$, Lewis$^a$ or Lewis$^b$ oligosaccharide, or derivatives thereof) can be used as inhibitory agents. Monoclonal antibodies to Lewis antigens, or derivatives thereof, are known in the art (e.g., mAbs to Le$^x$, Le$^y$, sialyl-Le$^x$ or sialyl-Le$^y$, from the Biomembrane Institute, Seattle, Wash., as described in Martensson, S., et al. (1995) *Hum. Pathol.* 26:735-739; and mAbs to Le$^a$ or sialyl-Le$^a$, as described in Kageshita, T., et al. (1995) *Cancer Res.* 55:1748-1751)

The ability of an inhibitory agent of the invention to inhibit production by immune cells of at least one cytokine that regulates a Th1 or Th2 response that normally occurs when the immune cell encounters a stimulatory form of a Lewis antigen can be evaluated using an in vitro culture system such as that described in the Examples. Cells (e.g., peripheral blood mononuclear cells) are cultured in the presence of both an inhibitory agent to be evaluated and a stimulatory agent as described in the preceding section (e.g., a sugar conjugate at a concentration of 100 μM) in a medium suitable for culture of the chosen cells. After a period of time (e.g., 24-72 hours), production of a cytokine that regulates development of a Th1 or Th2 response (e.g., IL-10 or IL-4) is assessed by determining the level of the cytokine in the culture supernatant as described in the preceding section. The ability of an inhibitory agent to inhibit cytokine production is evidenced by a lower level of cytokine in the supernatants of cells cultured in the presence of both the inhibitory agent and the stimulatory agent compared to the level of cytokine in the supernatant of cells cultured only in the presence of the stimulatory agent.

II. Pharmaceutical Compositions

Another aspect of the invention pertains to pharmaceutical compositions of the stimulatory or inhibitory agents of the invention. The pharmaceutical compositions of the invention typically comprise a stimulatory or inhibitory agent of the invention and a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, transdermal or oral administration. In a preferred embodiment, the composition is formulated such that it is suitable for intravenous administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, monostearate salts and gelatin. Moreover, the modulators can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Depending on the route of administration, the agent may be coated in a material to protect it from the action of enzymes, acids and other natural conditions which may inactivate the agent. For example, the agent can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan, et al., (1984) *J. Neuroimmunol* 7:27). Dispersions can also be prepared in glycerol, liquid polyethylene glycols, and mixtures thereof and in oils. Under ordinary conditions of storage and use, these preparations may contain a preservative to prevent the growth of microorganisms.

The active agent in the composition (i.e., a stimulatory or inhibitory agent of the invention) preferably is formulated in the composition in a therapeutically effective amount. A "therapeutically effective amount" refers to an amount effective, at dosages and for periods of time necessary, to achieve the desired therapeutic result, such as the development or progression of a Th2 or Th1 response to thereby influence the therapeutic course of a particular disease state. A therapeutically effective amount of an active agent may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. In another embodiment, the active agent is formulated in the composition in a prophylactically effective amount. A "prophylactically effective amount" refers to an amount effective, at dosages and for periods of time necessary, to achieve the desired prophylactic result, for example, influencing the development or progression of either a Th2 or Th1 response for prophylactic purposes. Typically, since a prophylactic dose is used in subjects prior to or at an earlier stage of disease, the prophylactically effective amount will be less than the therapeutically effective amount.

A non-limiting range for a therapeutically or prophylactically effective amounts of a stimulatory or inhibitory agent of the invention is 0.01 nM-20 mM. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

A stimulatory or inhibitory agent of the invention can be formulated into a pharmaceutical composition wherein the agent is the only active compound therein. Alternatively, the pharmaceutical composition can contain additional active compounds. For example, two or more stimulatory or inhibitory agents may be used in combination. Moreover, a stimulatory or inhibitory agent of the invention can be combined with one or more other agents that have immunomodulatory properties. For example, a stimulatory or inhibitory agent may be combined with one or more cytokines or adjuvants.

A pharmaceutical composition of the invention, comprising a stimulatory or inhibitory agent of the invention, can be administered to a subject to modulate immune responses (e.g., Th2 vs. Th1 responses) in the subject. As used herein, the term "subject" is intended to include living organisms in which an immune response can be elicited, e.g., mammals. Examples of subjects include humans, dogs, cats, mice, rats, and transgenic species thereof.

III. Modulation of Immune Responses

The invention provides immunomodulatory methods that can be used to influence the development of a Th1 or a Th2 response. In the methods of the invention, a cell (e.g., a human immune cell, a macrophage or a T cell) is contacted with an agent that modulates interaction of a compound comprising a Lewis antigen with the cell such that production by the cell of at least one cytokine that regulates development of a Th1 or Th2 response is modulated (i.e., stimulated or inhibited). The methods of the invention can be practiced either in vitro or in vivo. For practicing the method of the invention in vitro, cells can be obtained from a subject by standard methods and incubated (i.e., cultured) in vitro with a stimulatory or inhibitory agent of the invention to stimulate or inhibit, respectively, the production of at least one cytokine that regulates development of a Th1 or Th2 response. For example, peripheral blood mononuclear cells (PBMCs) can be obtained from a subject and isolated by density gradient centrifugation, e.g., with Ficoll/Hypaque. Specific cell populations can be depleted or enriched using standard methods. For example, monocytes/macrophages can be isolated by adherence on plastic. T cells or B cells can be enriched or depleted, for example, by positive and/or negative selection using antibodies to T cell or B cell surface markers, for example by incubating cells with a specific mouse monoclonal antibody (mAb), followed by isolation of cells that bind the mAb using anti-mouse-Ig coated magnetic beads. Monoclonal antibodies to cell surface markers are commercially available.

When a stimulatory agent is used in vitro, resulting in stimulation of the production of at least one cytokine that regulates Th1 or Th2 responses, the cytokine(s) can be recovered from the culture supernatant for further use. For example, the culture supernatant, or a purified fraction thereof, can be applied to T cells in culture to influence the development of Th1 or Th2 cells in vitro. Alternatively, the culture supernatant, or a purified fraction thereof, can be administered to a subject to influence the development of Th1 vs. Th2 responses in the subject. Moreover, cells treated in vitro with either a stimulatory or inhibitory agent can be administered to a subject to influence the development of a Th1 vs. Th2 response in the subject. For administration to a subject, it may be preferable to first remove residual agents in the culture from the cells before administering them to the subject. This can be done for example by a Ficoll/Hypaque gradient centrifugation of the cells.

For practicing the methods of the invention in vivo, a stimulatory or inhibitory agent is administered to a subject in a pharmacologically acceptable carrier (as described in the previous section) in amounts sufficient to modulate production of at least one cytokine that regulates development of a Th1 or Th2 response in the subject. A preferred route of administration for the agent is intravenous, although any route of administration suitable for achieving the desired immunomodulatory effect is contemplated by the invention.

The stimulatory methods of the invention (i.e., methods that use a stimulatory agent) result in production of at least one cytokine (preferably IL-10 or IL-4) which promotes development of a Th2 response and/or inhibits development of a Th1 response. Alternatively, the inhibitory methods of the invention (i.e., methods that use an inhibitory agent) inhibit the production of at least one cytokine (preferably IL-10 or IL-4) which promotes development of a Th2 response and/or inhibits development of a Th1 response. Thus, to apply a method of the invention to the treatment of a disease condition wherein a Th1 response is beneficial, an immunomodulatory method is selected that promotes such a Th1 response (while downregulating a Th2 response). Alternatively, to apply a method of the invention to the treatment of a disease condition wherein a Th2 response is beneficial, an immunomodulatory method is selected that promotes such a Th2 response (while downregulating a Th1 response). Application of the methods of the invention to the treatment of disease conditions may result in cure of the condition, a decrease in the type or number of symptoms associated with the condition, either in the long term or short term (i.e., amelioration of the condition) or simply a transient beneficial effect to the subject.

Numerous disease conditions associated with a predominant Th1 or Th2-type response have been identified and could benefit from modulation of the type of response mounted in the individual suffering from the disease condition. Application of the immunomodulatory methods of the invention to such diseases is described in further detail below.

A. Cancer

The inhibitory methods of the invention can be used to inhibit the production of cytokines that upregulate Th2 responses and downregulate Th1 responses in cancer patients, thereby promoting a Th1 response in the patients to ameliorate the course of the disease. The expression of Th2-promoting cytokines, in particular IL-10, has been reported to be elevated in cancer patients (see e.g., Yamamura, M., et al. (1993) *J. Clin. Invest.* 91:1005-1010; Pisa, P., et al. (1992) *Proc. Natl. Acad. Sci. USA* 89:7708-7712). Moreover, malignant cells have been reported to express tumor-associated antigens that comprise Lewis antigens (see e.g., Pauli, B. U., et al. (1992) *Trends in Glycoscience and Glycotechnology* 4:405-414; Hakomori, S-I. (1989) *Adv. Cancer Res.* 52:257-331; Martensson, S., et al. (1995) *Hum. Pathol.* 26:735-739; Kageshita, T., et al. (1995) *Cancer Res.* 55:1748-1751; Ohta, S., et al. (1995) *Immunol. Letters* 44:35-40). Still further, as demonstrated herein in Examples 2 and 3, peripheral blood mononuclear cells from patients with a variety of cancers (e.g., lung carcinoma, colon carcinoma or B lymphoma) respond to stimulation with Lewis antigen-protein carrier conjugates by producing IL-10. Thus, in the natural setting, stimulatory forms of Lewis antigens on tumor cells likely stimulate IL-10 production in cancer patients, thereby shifting the immune response toward a Th2 response and away from a Th1 response. This Th2 to Th1 shift can be counteracted by treating a cancer patient with an inhibitory agent of the invention to inhibit IL-10 production in the patient and promote a Th1 response.

A preferred inhibitory agent for inhibiting IL-10 production in human subjects comprises an inhibitory form of a Lewis$^y$ oligosaccharide or derivative thereof (e.g., soluble, free Le$^y$), although the particular Lewis antigen effective for inhibiting IL-10 production in individual cancer patients may vary for different patients and/or tumors (e.g., as shown in Examples 2 and 3, cells from two patients with B lymphoma and one patient with colon carcinoma responded preferentially to Le$^y$, whereas cells from one patient with B lymphoma responded preferentially to Le$^b$ and cells from one patient with lung carcinoma responded to Le$^x$). To determine which inhibitory agent is likely to be most effective for a particular cancer patient, it may be necessary first to determine which Lewis antigen is expressed on the tumor cells of the patient (e.g., by reacting a sample of tumor cells in vitro with a panel of mAbs that bind to different Lewis antigens) and/or which Lewis antigen the cells from the cancer patient preferentially respond to in vitro (e.g., by culturing PBMCs from the cancer patient in vitro with various stimulatory forms of Lewis antigens in an assay as described in the Examples). Based on these in vitro tests, an appropriate inhibitory agent can be selected that, when administered to the cancer patient, will block the stimulation of IL-10 production that results when cells of the cancer patient encounter Lewis antigens on tumor cells in vivo.

B. Infectious Disease

The inhibitory methods of the invention also can be used to inhibit the production of cytokines that upregulate Th2 responses and downregulate Th1 responses in patients with infectious diseases, thereby promoting a Th1 response in the patients to ameliorate the course of the disease. The expression of Th2-promoting cytokines, in particular IL-10, has been reported to increase during a variety of infections, including HIV infection, tuberculosis, leishmaniasis, schistosomiasis, filarial nematode infection and intestinal nematode infection (see e.g.; Shearer, G. M. and Clerici, M. (1992) *Prog. Chem. Immunol.* 54:21-43; Clerici, M and Shearer, G. M. (1993) *Immunology Today* 14:107-111; Fauci, A. S. (1988) *Science* 239:617-623; Locksley, R. M. and Scott, P. (1992) *Immunoparasitology Today* 1:A58-A61; Pearce, E. J., et al. (1991) *J. Exp. Med.* 173:159-166; Grzych, J-M., et al. (1991) *J. Immunol.* 141:1322-1327; Kullberg, M. C., et al. (1992) *J. Immunol.* 148:3264-3270; Bancroft, A. J., et al. (1993) *J. Immunol.* 150:1395-1402; Pearlman, E., et al. (1993) *Infect. Immun.* 61:1105-1112; Else, K. J., et al. (1994) *J. Exp. Med.* 179:347-351) and is associated with a Th1 to Th2 shift. Infected cells and/or proteins from infectious agents have been reported to express Lewis antigens. For example, the Lewis$^y$ oligosaccharide has been reported to be expressed by HIV-infected cells (Adachi, M., et al. (1988) *J. Exp. Med.* 167:323-331). Schistosome egg antigen expresses the Lewis$^x$ oligosaccharide (Ko, A., et al. (1987) *Proc. Natl. Acad. Sci. USA* 87:4159-4163). Liver cells in chronic active hepatitis express the Lewis$^y$ oligosaccharide (Muguruma, M, et al. (1994) *Anatomic Pathology* 102:176-181), while Kupffer cells express sialyl oligomeric Lewis$^x$ (Okado, Y. and Tsuji, T. (1990) *Lancet* 335:1302-1307). Thus, during the course of various natural infection, stimulatory forms of Lewis antigens on infected cells and/or expressed by proteins of the infectious agent likely stimulate IL-10 production in the infected subject, thereby shifting the immune response toward a Th2 response and away from a Th1 response. This Th2 to Th1 shift can be counteracted by treating the infected subject with an inhibitory agent of the invention to inhibit IL-10 production in the infected subject and promote a Th1 response (similar to the approach described above for treating cancer patients). The inhibitory agent that is likely to be most effective for treatment of a particular infection can be determined by approaches similar to those described above for selecting inhibitory agents to treat cancer patient (for example, the type of Lewis antigen expressed by infected cells and/or proteins of the infectious agent can be determined and/or one can determine which Lewis antigen the cells from the subject preferentially respond to in vitro).

C. Allergies:

Allergies are mediated through IgE antibodies whose production is regulated by the activity of Th2 cells and the cytokines produced thereby. In allergic reactions, IL-4 is produced by Th2 cells, which further stimulates production of IgE antibodies and activation of cells that mediate allergic reactions, i.e., mast cells and basophils. IL-4 also plays an important role in eosinophil mediated inflammatory reactions. As demonstrated in Example 2, T cells from a patient allergic to pollen respond to stimulation with stimulatory forms of Lewis antigens by producing IL-10. Production of IL-10 in allergic patients may promote a Th2 response and downregulates a Th1 response, thereby exacerbating the allergic condition. An allergic subject can be treated with an inhibitory agent of the invention to inhibit IL-10 production in the subject and shift the immune response away from a Th2 response and toward a Th1 response as a means to alleviate the allergic condition.

Allergic reactions may be systemic or local in nature, depending on the route of entry of the allergen and the pattern of deposition of IgE on mast cells or basophils. Thus, for treatment of an allergic subject, an inhibitory agent of the invention can be administered either systemically or locally. Moreover, it may be beneficial to coadminister to the subject the allergen together with the inhibitory agent to inhibit (e.g., desensitize) the allergen-specific response.

D. Autoimmune Diseases:

The methods of the invention also can be used therapeutically for treating autoimmune diseases which are associated with a Th1- or Th2-type dysfunction. Many autoimmune disorders are the result of inappropriate activation of T cells that are reactive against self tissue and that promote the production of cytokines and autoantibodies involved in the pathology of the diseases. It has been shown that modulation of T helper-type responses can either have a beneficial or detrimental effect on an autoimmune disease. For example, in experimental allergic encephalomyelitis (EAE), stimulation of a Th2-type response by administration of IL-4 at the time of the induction of the disease diminishes the intensity of the autoimmune disease (Paul, W. E., et al. (1994) *Cell* 76:241-251). Furthermore, recovery of the animals from the disease has been shown to be associated with an increase in a Th2-type response as evidenced by an increase of Th2-specific cytokines (Koury, S. J., et al. (1992) *J. Exp. Med.* 176:1355-1364). Moreover, T cells that can suppress EAE secrete Th2-specific cytokines (Chen, C., et al. (1994) *Immunity* 1:147-154). Since stimulation of a Th2-type response in EAE has a protective effect against the disease, stimulation of a Th2 response in subjects with multiple sclerosis (for which EAE is a model) may be beneficial therapeutically.

Similarly, stimulation of a Th2-type response in type I diabetes in mice provides a protective effect against the disease. Indeed, treatment of NOD mice with IL-4 (which promotes a Th2 response) prevents or delays onset of type I diabetes that normally develops in these mice (Rapoport, M. J., et al. (1993) *J. Exp. Med.* 178:87-99). Thus, stimulation of a Th2 response in a subject suffering from or susceptible to diabetes may ameliorate the effects of the disease or inhibit the onset of the disease.

Yet another autoimmune disease in which stimulation of a Th2-type response may be beneficial is rheumatoid arthritis (RA). Studies have shown that patients with rheumatoid arthritis have predominantly Th1 cells in synovial tissue (Simon, A. K., et al., (1994) *Proc. Natl. Acad Sci. USA* 91:8562-8566). By stimulating a Th2 response in a subject with RA, the detrimental Th1 response can be concomitantly downmodulated to thereby ameliorate the effects of the disease.

To treat an autoimmune disease in which a Th2-type response is beneficial to the course of the disease in the subject, a stimulatory agent of the invention can be administered to the subject in amounts sufficient to stimulate a Th2-type response. The stimulatory agent can be used alone, or in combination with one or more additional agents that promote Th2 responses (e.g., Th2-promoting cytokines, such as IL-4 or IL-10). Depending on the disease, the stimulatory agent may be administered either systemically or locally. For example in the case of rheumatoid arthritis, the agent may be administered directly into the joints. For systemic treatment, the stimulatory agent preferably is administered intravenously. Alternative to direct administration of the stimulatory agent to the subject, autoimmune diseases may be treated by an ex vivo approach. In this case, immune cells (e.g., T cells, macrophages and/or B cells) are obtained from a subject having an autoimmune disease, cultured in vitro with a stimulatory agent of the invention to stimulate production by the cells of one or more cytokines that promote a Th2 response (e.g., IL-10), followed by readministration of the cells to the subject.

In contrast to the autoimmune diseases described above in which a Th2 response is desirable, other autoimmune diseases may be ameliorated by a Th1-type response. Such diseases can be treated using an inhibitory agent of the invention (as described above for cancer and infectious diseases). The treatment may be further enhanced by administrating a Th1-promoting cytokine (e.g., IFN-γ) to the subject in amounts sufficient to further stimulate a Th1-type response.

The efficacy of agents for treating autoimmune diseases can be tested in the above described animal models of human diseases (e.g., EAE as a model of multiple sclerosis and the NOD mice as a model for diabetes) or other well characterized animal models of human autoimmune diseases. Such animal models include the mrl/lpr/lpr mouse as a model for lupus erythematosus, murine collagen-induced arthritis as a model for rheumatoid arthritis, and murine experimental myasthenia gravis (see Paul ed., *Fundamental Immunology*, Raven Press, New York, 1989, pp. 840-856). A modulatory (i.e., stimulatory or inhibitory) agent of the invention is administered to test animals and the course of the disease in the test animals is then monitored by the standard methods for the particular model being used. Effectiveness of the modulatory agent is evidenced by amelioration of the disease condition in animals treated with the agent as compared to untreated animals (or animals treated with a control agent).

Non-limiting examples of autoimmune diseases and disorders having an autoimmune component that may be treated according to the invention include diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

E. Inflammatory Bowel Disease in Infants

The methods and compositions of the invention also can be used to downregulate inflammatory immune responses in the bowel in newborn infants. The largest biological source for Lewis-antigen containing oligosaccharides is human breast milk and breast fed babies have a lower incidence of diarrhea and colitis/inflammatory bowel disease. Commercially available formula was tested for the presence of Lewis antigen-containing sugars by ELISA and was found not to contain detectable amounts of these sugars, nor did the ingredients list these sugars as additives. Nonfat dry milk was listed as an additive to the formula but when non-fat dry milk was tested for the presence of Lewis antigen-containing sugars by ELISA, again none were detected. Thus, Lewis antigen-containing compounds as described herein can be added to commercial baby formulas and administered to infants orally to inhibit diarrhea and colitis/inflammatory bowel disease. Accordingly, the invention provides an infant formula comprising one or more Lewis antigen-containing compounds as an additive.

In addition to the foregoing disease situations, the immunomodulatory methods of the invention also are useful for other purposes. For example, the stimulatory methods of the invention (i.e., methods using a stimulatory agent) can be used to stimulate production of Th2-promoting cytokines (such as IL-10 or IL-4) in vitro for commercial production of these cytokines (e.g., cells can be cultured with a stimulatory agent in vitro to stimulate IL-10 or IL-4 production and the IL-10 or IL-4 can be recovered from the culture supernatant, further purified if necessary, and packaged for commercial use).

Furthermore, the immunomodulatory methods of the invention can be applied to vaccinations to promote either a Th1 or a Th2 response to an antigen of interest in a subject. That is, the agents of the invention can serve as adjuvants to direct an immune response to a vaccine either to a Th1 response or a Th2 response. For example, to stimulate an antibody response to an antigen of interest (i.e., for vaccination purposes), the antigen and a stimulatory agent of the invention can be coadministered to a subject to promote a Th2 response to the antigen in the subject, since Th2 responses provide efficient B cell help and promote IgG1 production. Alternatively, to promote a cellular immune response to an antigen of interest, the antigen and an inhibitory agent of the invention can be coadministered to a subject to promote a Th1 response to the antigen in a subject, since Th1 responses favor the development of cell-mediated immune responses (e.g., delayed hypersensitivity responses). The antigen of interest and the modulatory agent can be formulated together into a single pharmaceutical composition or in separate compositions. In a preferred embodiment, the antigen of interest and the modulatory agent are administered simultaneously to the subject. Alternatively, in certain situations it may be desirable to administer the antigen first and then the modulatory agent or vice versa (for example, in the case of an antigen that naturally evokes a Th1 response, it may be beneficial to first administer the antigen alone to stimulate a Th1 response and then administer a stimulatory agent, alone or together with a boost of antigen, to shift the immune response to a Th2 response).

This invention is further illustrated by the following examples which should not be construed as limiting. The contents of all references, patents and published patent applications cited throughout this application are hereby incorporated by reference.

EXAMPLE 1

In this example, the ability of macrophages to produce IL-10 upon stimulation with various oligosaccharide conjugates was examined. Granuloma macrophages were prepared from C57BL/6 mice as described in Flores Villanueva, P. O., et al. (1994) *J. Immunol.* 153:5190-5199 and Flores Villanueva, P. O., et al. (1994) *J. Immunol.* 152:1847-1855. Two million cells in 1 ml of DMEM, 10% FCS were incubated with either no stimulant (i.e., medium alone; a negative control), lipopolysaccharide (LPS; at 20 μg/ml; a positive control), schistosome egg antigen (SEA; at 10 μg/ml), various sugars conjugated to human serum albumin (at 100 μg/ml) or human serum albumin alone (HSA; at 100 μg/ml; a negative control). The sugar conjugates tested were lacto-N-fucopentaose III (LNFP-III), lacto-N-neotetraose (LNT) and Lewis$^y$ (Le$^y$). The oligosaccharide conjugates were obtained from Accurate Chemicals, Westbury, N.Y.

At various time points (24, 48 and 72 hours), the level of IL-10 in the supernatant was determined by two-site ELISA as described by Kullberg, et al. (*J. Immunol.* (1982) 148: 3264-3270). Briefly, polystyrene microtiter plates (Costar) were coated with IL-10-specific monoclonal antibodies (clone SXC-1; DNAX Corp.). Culture supernatants were incubated on the antibody-coated plates and then probed with biotinylated antibody. Serial dilutions of recombinant mouse IL-10 (PharMingen) were assayed simultaneously to construct a standard curve for relative IL-10 concentration. To detect the biotinylated antibody bound to IL-10, avidin-peroxidase conjugate (Sigma Chemical Corp., St. Louis, Mo.) was diluted in phosphate buffered saline (PBS)/10% fetal calf serum and added to the wells for 30 minutes at room temperature. The plates were washed with PBS/0.5% Tween 20 (Fisher), and then tetramethylbenzidine substrate (Kirkegaard & Perry Laboratories) was added; the reaction was stopped with 0.4 M phosphoric acid and read at 450 nm in a UvMax Reader (Molecular Devices).

The results are shown below in Table I.

TABLE I

IL-10 Secretion by Granuloma Macrophages

| STIMULANTS | IL-10 LEVEL (PG/ML) | | |
|---|---|---|---|
| | 24 HR | 48 HR | 72 HR |
| Medium | 898 | 1510 | 871 |
| LPS | 7864 | 6559 | 4555 |
| SEA | 2805 | 2282 | 2835 |
| HSA-LNFP-III | 1967 | 1682 | 1211 |
| HSA-LNT | 1038 | 1298 | 912 |
| HSA-LeY | 3860 | 3955 | 3076 |
| HSA | 1247 | 1214 | 1089 |

The greatest response was observed with the Lewis$^y$ conjugate as the stimulant. A less vigorous response was seen with SEA and the LNFP-III conjugate, both of which expresses the Lewis$^x$ antigen. No response was seen with the LNT conjugate. The results shown in Table I indicate that granuloma macrophages can produce IL-10 upon stimulation with compounds comprising a Lewis antigen, in particular a Lewis$^y$ antigen.

EXAMPLE 2

In this example, the ability of peripheral blood mononuclear cells (PBMCs) from humans suffering from various disorders to produce IL-10 upon stimulation with various oligosaccharide conjugates was examined. Human PBMCs were obtained from: 1) an individual who was allergic to pollen; 2) an individual suffering from lung carcinoma and 3) an individual suffering from colon carcinoma. One million PBMC in RPMI-1640 medium containing 10% human AB serum were incubated with either no stimulant (i.e., medium alone; a negative control), lipopolysaccharide (LPS; at 20 µg/ml; a positive control), various sugars conjugated to human serum albumin (at 100 µg/ml) or human serum albumin alone (HSA; at 100 µg/ml; a negative control). The sugar conjugates tested were lacto-N-fucopentaose I (LNFP-I), lacto-N-fucopentaose III (LNFP-III), lacto-N-neotetraose (LNT) and Lewis$^y$ (Le$^y$).

After 24 hours, the level of IL-10 (in pg/ml) in the supernatant was determined by two-site ELISA as described by in Example 1, using an anti-human IL-10 monoclonal antibody obtained from PharMingen. Additionally, cellular proliferation was measured by standard $^3$H-thymidine uptake at 90 hours.

The results are shown below in Table II.

TABLE II

Responses of Human Cells from Allergic or Cancer Patients to Various Sugar Conjugates

| STIMULANT | POLLEN ALLERGIC | | LUNG CARCINOMA | | COLON CARCINOMA | |
|---|---|---|---|---|---|---|
| | CPM | IL-10 | CPM | IL-10 | CPM | IL-10 |
| Medium | 649 | 160 | 143 | 1200 | 30 | 0 |
| LPS | 1946 | 906 | 232 | 1400 | 222 | 8221 |
| HSA-LNFP-I | 490 | <u>432</u> | 3452 | <u>10000</u> | 423 | <u>347</u> |
| HSA-LNFP-III | 1456 | <u>442</u> | 137 | 1000 | 270 | <u>202</u> |
| HSA-LNT | 1133 | <u>220</u> | 141 | 1000 | 186 | <u>304</u> |
| HSA-LeY | 5960 | <u>736</u> | 458 | 1200 | 934 | <u>689</u> |
| HSA | 460 | 166 | 152 | 1200 | 141 | 0 |

The greatest response by cells of the pollen allergic individual was observed with the Lewis$^y$ conjugate as the stimulant. Less vigorous responses were seen with the LNFP-I and LNFP-III conjugates. A minimal response was seen with the LNT conjugate. The greatest response by cells of the individual suffering from colon carcinoma also was observed with the Lewis$^y$ conjugate as the stimulant. Less vigorous responses were seen with the LNFP-I, LNFP-III and LNT conjugates. For the individual with lung carcinoma, a vigorous response was observed only with the LNFP-I conjugate. The results shown in Table II indicate that human PBMCs from individuals suffering from various disorders (e.g., allergies or cancers) can produce IL-10 upon stimulation with compounds comprising a Lewis antigen.

EXAMPLE 3

In this example, the ability of peripheral blood mononuclear cells (PBMCs) from three humans with B lymphomas to produce IL-10 upon stimulation with various oligosaccharide conjugates was examined. One million PBMC in RPMI-1640 medium containing 10% human AB serum were incubated with either no stimulant (i.e., medium alone; a negative control), lipopolysaccharide (LPS; at 20 µg/ml; a positive control), various sugars conjugated to human serum albumin (at 100 µg/ml) or human serum albumin alone (HSA; at 100 µg/ml; a negative control). The sugar conjugates tested were lacto-N-fucopentaose I (LNFP-I), lacto-N-fucopentaose III (LNFP-III), lacto-N-neotetraose (LNT), Lewis$^y$ (Le$^y$) and lacto-N-difucohexose I (LND).

After 24 hours, the level of IL-10 (in pg/ml) in the supernatant was determined by two-site ELISA as described by in Example 2. Additionally, cellular proliferation was measured by standard $^3$H-thymidine uptake at 90 hours.

The results are shown below in Table III.

TABLE III

Responses of Human PBMC from B Lymphoma Patients to Various Sugar Conjugates

| STIMULANT | B-LYMPHOMA-1 | | B-LYMPHOMA-2 | | B-LYMPHOMA-3 | |
|---|---|---|---|---|---|---|
| | CPM | IL-10 | CPM | IL-10 | CPM | IL-10 |
| Medium | 444 | 814 | 288 | 0 | 1710 | 0 |
| LPS | 80424 | 6053 | 1084 | 201 | 3424 | 1049 |
| HSA-LNFP-I | 889 | <u>2422</u> | 970 | 0 | 4504 | 0 |
| HSA-LNFP-III | 459 | <u>4386</u> | 1009 | 0 | 3425 | <u>64</u> |
| HSA-LNT | 444 | <u>1081</u> | 731 | 0 | 3530 | <u>39</u> |
| HSA-LeY | 6211 | <u>6786</u> | 1099 | 2 | 5838 | <u>210</u> |
| HSA-LND | 1214 | <u>3521</u> | 502 | <u>307</u> | 4324 | 0 |
| HSA | 248 | 945 | 660 | 0 | 3149 | 0 |

The greatest response by cells of the B-lymphoma-1 patient was observed with the Lewis$^y$ conjugate as the stimulant. Less vigorous responses were seen with the LNFP-I, LNFP-III and LND conjugates. Similarly, the greatest response by cells of the B-lymphoma-3 patient was observed with the Lewis$^y$ conjugate as the stimulant. Less vigorous responses were seen with the LNFP-III and LNT conjugates. For the B-lymphoma-2 patient, a vigorous response was observed only with the LND conjugate, which expresses the Lewis$^b$ oligosaccharide. The results shown in Table III indicate that human PBMCs from individuals suffering from B lymphomas can produce IL-10 upon stimulation with compounds comprising a Lewis antigen.

EXAMPLE 4

In this example, the ability of splenocytes from uninfected mice or mice infected with *S. mansoni* to produce IL-10 or IL-4 was examined upon stimulation of the cells with various oligosaccharide conjugates having different sugar densities. In particular, the stimulatory ability of LNFP III-HSA (which comprises the Lewis$^x$ antigen) was compared to conjugates of Lewis$^a$ antigen, Lewis$^x$ antigen, sialyl-Lewis$^x$ antigen or sialyl-Lewis$^a$ antigen to a polyacrylamide (PAA) carrier molecule. The PAA conjugates (obtained from GlycoTech, Rockville, Md.) have a ligand density approximately 5-6 fold higher than that of the HSA conjugate. Within the LNFP III-HSA conjugate, approximately 10-12 sugar molecules/HSA molecule are present. The total conjugate weight is 67 kD, of which the LNFP III molecules comprise approximately 3.5-4.0% of the total weight. Thus, when 50 µg/ml of LNFP III-HSA conjugate is used for stimulation, the actual concentration of sugar used is between 1.5 and 2.0 µg/ml. Within the polyacrylamide conjugates, approximately 25-30 sugar molecules/PAA molecule are present. The total conjugate is approximately 30 kD, of which the Lewis antigens comprise approximately 20-24% of the total weight. Thus, when 50 µg/ml of Lewis antigen-PAA conjugate is used for stimulation, the actual concentration of sugar used is approximately 10-12 µg/ml.

In these experiments unfractionated splenocytes isolated from 7-week *S. mansoni*-infected CBA/J mice or uninfected mice were used. The splenocytes were incubated either with media alone, Con A (50 µg/ml), LPS (50 µg/ml), anti-IgM (25 µg/ml) (all as controls), SEA (5-10 µg/ml), HSA-LNFP III (50 µg/ml), Lewis$^a$-PAA (2, 10 or 50 µg/ml), Lewis$^x$-PAA (2, 10 or 50 µg/ml), sialyl-Lewis$^x$-PAA (2, 10 or 50 µg/ml) or sialyl-Lewis$^a$-PAA (2, 10 or 50 µg/ml).

Figure 2:
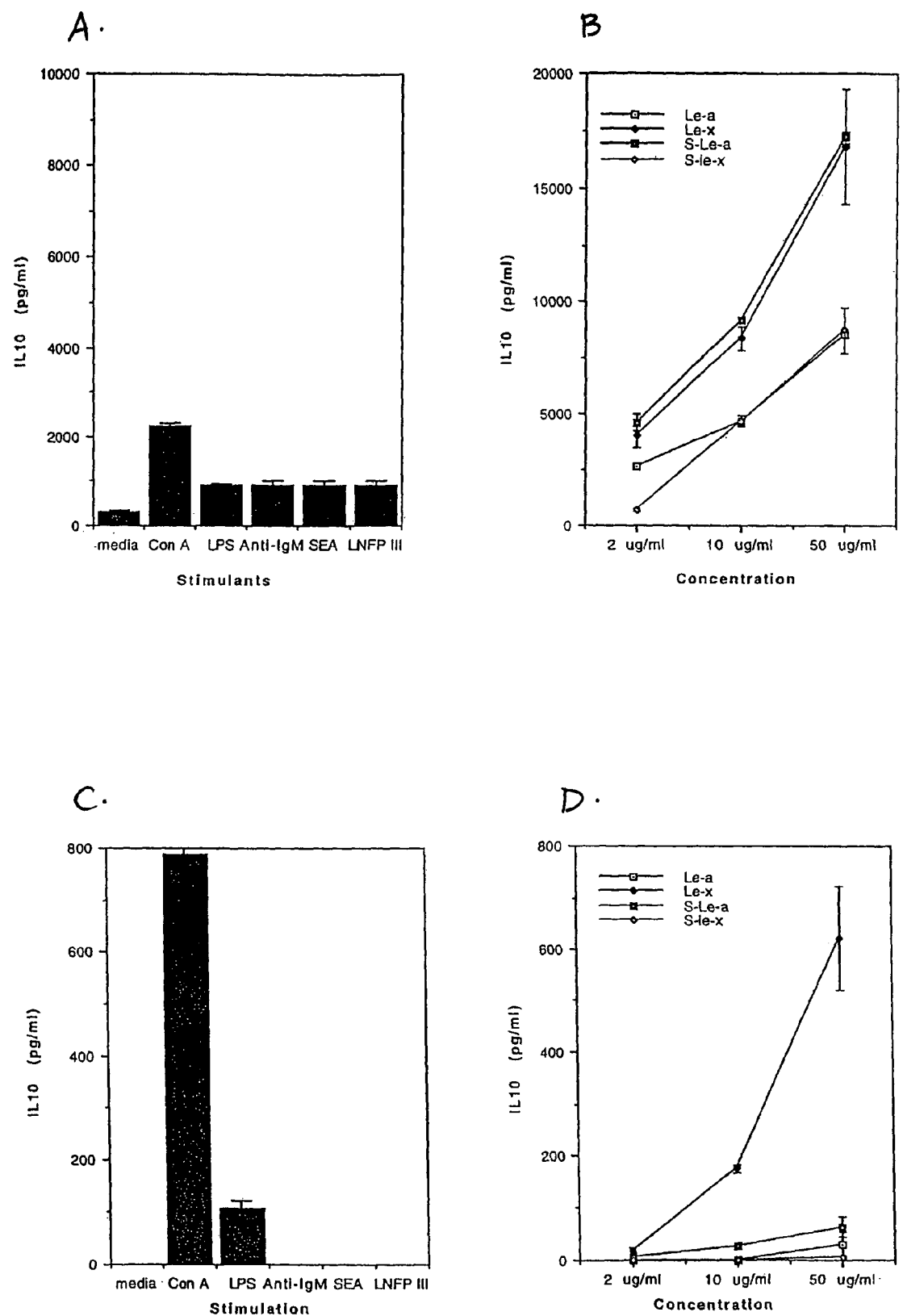
FIG. 2A is a bar graph depicting the production of IL-10 by splenocytes from S. mansoni infected mice when stimulated with either media alone, Con A, LPS. anti-IgM, SEA or LNFP III conjugated to HSA.
FIG. 2B is a graph depicting the production of IL-10 by splenocytes from S. mansoni infected mice when stimulated with increasing amounts of either $Lewis^a$ antigen, $Lewis^x$ antigen, sialyl-$Lewis^x$ antigen or sialyl-$Lewis^a$ antigen, each conjugated to polyacrylamide.
FIG. 2C is a bar graph depicting the production of IL-10 by splenocytes from uninfected mice when stimulated with either media alone, Con A, LPS. anti-IgM, SEA or LNFP III conjugated to HSA.
FIG. 2D is a graph depicting the production of IL-10 by splenocytes from uninfected mice when stimulated with increasing amounts of either $Lewis^a$ antigen, $Lewis^x$ antigen, sialyl-$Lewis^x$ antigen or sialyl-$Lewis^a$ antigen, each conjugated to polyacrylamide.

Proliferation of the splenocytes was assessed by standard tritiated thymidine uptake. The results are shown in FIGS. 1A, 1B, 1C and 2D. Lewis$^a$, Lewis$^x$, sialyl-Lewis$^x$ and sialyl-Lewis$^a$, each conjugated to PAA, did not stimulate proliferation of the splenocytes from either infected or uninfected mice.

The level of IL-10 production was assessed as described in Example 1. The results are shown in FIGS. 2A, 2B, 2C and 2D. Lewis$^a$, Lewis$^x$, sialyl-Lewis$^x$ and sialyl-Lewis$^a$, each conjugated to PAA, were able to stimulate IL-10 production by splenocytes from infected mice and were substantially more effective at stimulating IL-10 production than LNFP III-HSA (compare FIG. 2A and FIG. 2B). For example, 50 µg/ml of LNFP III-HSA stimulated the production of approximately 1000 pg/ml of IL-10 (see FIG. 2A), whereas the same amount of Lewis$^x$-PAA and sialyl-Lewis$^a$-PAA stimulated production of approximately 17,500 pg/ml of IL-10 and the same amount of Lewis$^a$-PAA and sialyl-Lewis$^x$-PAA stimulated production of approximately 7,500 pg/ml of IL-10 (see FIG. 2B). Lewis$^x$-PAA was also able to stimulated IL-10 production by splenocytes from uninfected mice (e.g., production of approximately 600 pg/ml of IL-10 was stimulated by 50 µg/ml of Lewis$^x$-PAA, whereas the same amount of LNFP III-HSA did not stimulate IL-10 production by splenocytes from uninfected mice; compare FIGS. 2C and 2D).

Figure 3:
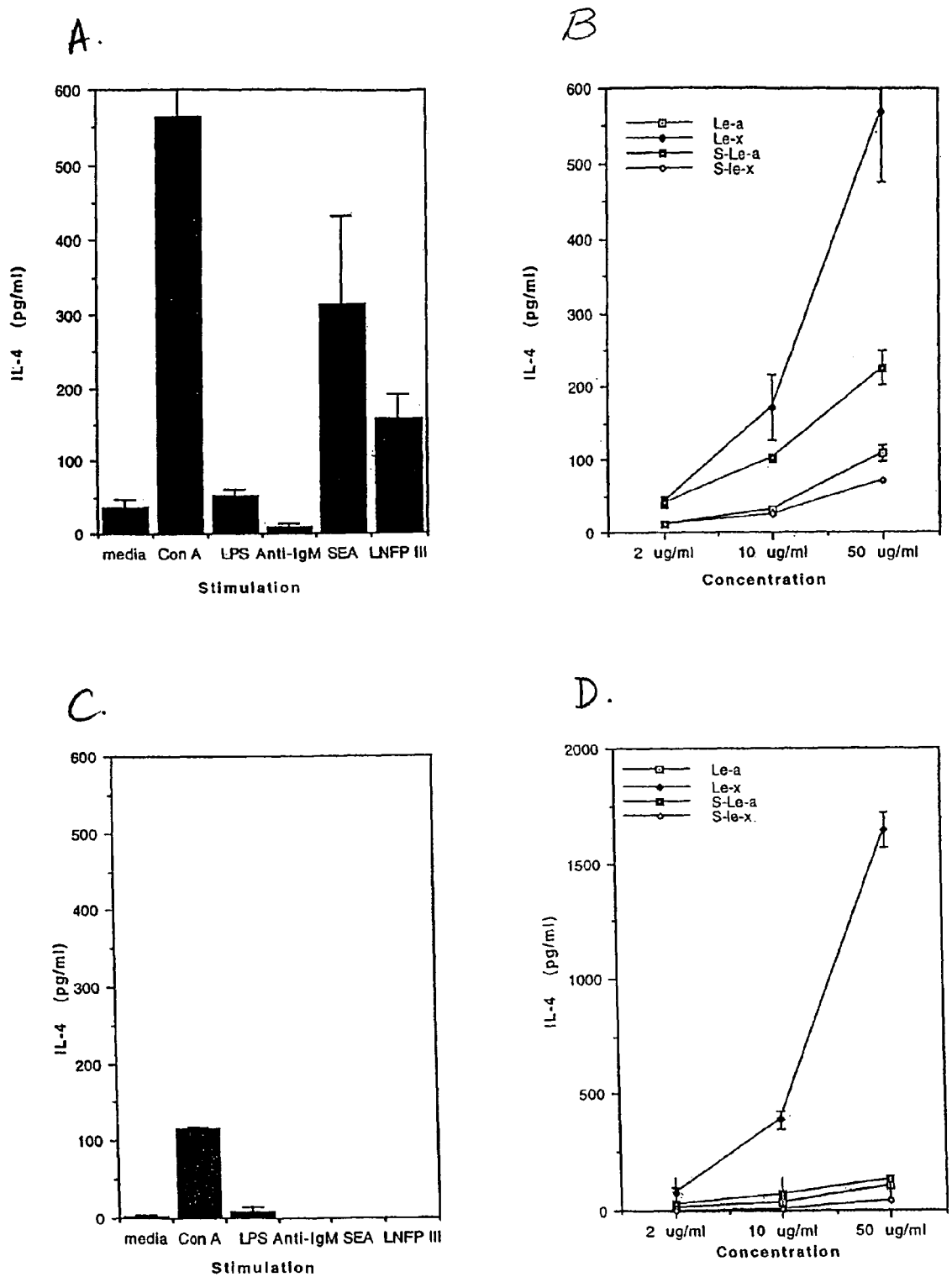
FIG. 3A is a bar graph depicting the production of IL-4 by splenocytes from S. mansoni infected mice when stimulated with either media alone, Con A, LPS. anti-IgM, SEA or LNFP III conjugated to HSA.
FIG. 3B is a graph depicting the production of IL-4 by splenocytes from S. mansoni infected mice when stimulated with increasing amounts of either $Lewis^a$ antigen, $Lewis^x$ antigen, sialyl-$Lewis^x$ antigen or sialyl-$Lewis^a$ antigen, each conjugated to polyacrylamide.
FIG. 3C is a bar graph depicting the production of IL-4 by splenocytes from uninfected mice when stimulated with either media alone, Con A, LPS. anti-IgM, SEA or LNFP III conjugated to HSA.
FIG. 3D is a graph depicting the production of IL-4 by splenocytes from uninfected mice when stimulated with increasing amounts of either $Lewis^a$ antigen, $Lewis^x$ antigen, sialyl-$Lewis^x$ antigen or sialyl-$Lewis^a$ antigen, each conjugated to polyacrylamide.

The level of IL-4 production in the cultures was assessed by a standard ELISA using an anti-mouse IL-4 monoclonal antibody obtained from PharMingen. The results are shown in FIGS. 3A, 3B, 3C and 3D. The Lewis$^x$-PAA was effective at stimulating IL-4 production by splenocytes from both uninfected and infected mice (see FIGS. 3B and 3D). Sialyl-Lewis$^a$-PAA stimulated lower amounts of IL-4 production in splenocytes from infected mice (see FIG. 3B), as did LNFP III-HSA (see FIG. 3A), whereas these conjugates did not stimulate IL-4 production by splenocytes from uninfected mice (see FIGS. 3C and 3D).

These results demonstrate that Lewis antigen-containing sugar conjugates, in particular those with a high sugar density, can stimulate IL-10 and IL-4 production by naive splenocytes (i.e., splenocytes from uninfected mice). In particular, IL-4 production was greater by stimulated naive splenocytes than stimulated splenocytes from infected mice. This IL-4 production likely is not by B cells. Rather this IL-4 production is likely by T cells and/or other non-T, non-B cells (e.g., mast cells, basophils and/or eosinophils).

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of stimulating a Th2 response in a subject comprising administering to the subject multivalent LNFPIII in an amount sufficient to stimulate a Th2 response.

2. The method of claim 1, wherein the subject has an autoimmune disease.

3. The method of claim 2, wherein the autoimmune disease is diabetes.

4. The method of claim 2, wherein the autoimmune disease is arthritis.

5. The method of claim 2, wherein the autoimmune disease is multiple sclerosis.

6. The method of claim 2, wherein the autoimmune disease is colitis.

7. The method of claim 2, wherein the autoimmune disease is psoriasis.

8. The method of claim 1, wherein the multivalent LNFPIII is conjugated to a carrier molecule.

9. The method of claim 8, wherein the multivalent LNFPIII represents approximately 10-25% of the conjugate by weight.

10. The method of claim 8, wherein the multivalent LNFPIII represents approximately 15-25% of the conjugate by weight.

11. The method of claim 8, wherein the LNFPIII represents approximately 20-25% of the conjugate by weight.

12. The method of claim 8, wherein the conjugate comprises at least 10-12 molecules of the LNFPIII.

13. The method of claim 8, wherein the conjugate comprises at least 25-30 molecules of the LNFPIII.

14. The method of claim 1, wherein the LNFPIII is administered orally.

15. The method of claim 1, wherein the LNFPIII or derivative thereof is administered intravenously.

16. The method of claim 1, wherein the multivalent LNFPIII is administered intramuscularly.

17. The method of claim 1, wherein the LNFPIII is administered subcutaneously.

18. A method of treating an autoimmune disease in a subject comprising administering a multivalent conjugate comprising at least 10-12 molecules of LNFPIII crosslinked to a carrier molecule in an amount sufficient to ameliorate the autoimmune disease.

* * * * *